United States Patent [19]

Mizoguchi

[11] Patent Number: 4,502,126
[45] Date of Patent: Feb. 26, 1985

[54] APPARATUS FOR DETECTING AN AMOUNT OF LIQUID REMAINED IN A VESSEL

[75] Inventor: Fumio Mizoguchi, Hachioji, Japan

[73] Assignee: Olympus Optical Co., Ltd., Tokyo, Japan

[21] Appl. No.: 379,478

[22] Filed: May 18, 1982

[30] Foreign Application Priority Data

May 21, 1981 [JP] Japan ............................ 56-72793[U]

[51] Int. Cl.³ ............................................ G01F 13/00
[52] U.S. Cl. .............................. 364/509; 33/126.7 A; 73/304 R; 222/23; 364/562
[58] Field of Search ............... 364/509, 561, 562, 550, 364/551, 496, 497, 552; 377/2, 19, 21; 340/603, 612, 615, 618, 620; 137/386, 393, 558; 73/447, 290 R, 290 B, 291, 294, 305, 304 R, 304 C, 313, 314; 33/126, 126.7 R, 126.7 A; 222/23

[56] References Cited

U.S. PATENT DOCUMENTS

| | | | |
|---|---|---|---|
| 2,380,436 | 7/1945 | Holdman | 33/126.7 A |
| 2,382,516 | 8/1945 | Sprague | 33/126.7 A |
| 2,657,577 | 11/1953 | Falk | 73/314 X |
| 3,474,902 | 10/1969 | Putman | 73/290 R X |
| 3,566,478 | 3/1971 | Hurlston | 33/126 |
| 3,895,356 | 7/1975 | Kraus | 364/562 |
| 3,969,941 | 7/1976 | Rapp | 73/290 R |
| 4,166,609 | 9/1979 | Nagasaki et al. | 73/304 R |
| 4,360,128 | 11/1982 | Neumann | 340/618 |
| 4,386,406 | 5/1983 | Igarashi et al. | 73/313 |
| 4,402,048 | 8/1983 | Tsuchida et al. | 364/509 |

Primary Examiner—Errol A. Krass
Assistant Examiner—Edward R. Cosimano
Attorney, Agent, or Firm—Parkhurst & Oliff

[57] ABSTRACT

An amount of a reagent remaining in a reagent bottle is detected by measuring a distance along which a delivery nozzle is moved downward from a reference level until the tip of nozzle is immersed into the reagent. The distance is measured by counting clock pulses supplied from an oscillating unit which produces the clock pulses during a time interval from the initial downward movement of the nozzle to an instant when the nozzle tip is immersed into the liquid. A count value is compared with a predetermined maximum count value by a comparing unit to derive a difference therebetween. The difference thus derived indicates a residual amount of the liquid. The number of times by which the liquid may be delivered is obtained by dividing the detected residual amount by a unit amount which is delivered by a single delivery operation.

13 Claims, 6 Drawing Figures

FIG.5

| | | | | | |
|---|---|---|---|---|---|
| 19a | GOT | GPT | TP | ALB | CRE |
| 19b | 50 | 40 | 110 | 65 | 30 |
| 19c | – | – | 80 | 0 | – |

FIG.6

| | | | | | |
|---|---|---|---|---|---|
| 19a | 1 | 2 | 3 | 4 | 5 |
| 19b | 50 | 40 | 110 | 80 | 65 |

# APPARATUS FOR DETECTING AN AMOUNT OF LIQUID REMAINED IN A VESSEL

BACKGROUND OF THE INVENTION

The present invention relates to an apparatus for detecting an amount of a liquid contained in a bottle to be delivered by a delivery nozzle, and more particularly to an apparatus for detecting amounts of different kinds of reagents remaining in reagent vessels for use in an automatic chemical analyzer.

Various types of automatic chemical analyzers have been developed and practiced. They may be roughly classified into two types on account of a manner of treating one or more reagents. In the first type of analyzer, required reagents are set in the analyzer every day, and in the second type of analyzer the reagents are reserved in a refrigerator installed in the analyzer. Recently, the second type of analyzer has become popular because the reagents can be handled or managed easily. In such an analyzer, it is necessary to monitor or detect amounts of the reagents remained in reagent bottles at the beginning of an analysis or during the analysis, and when a residual amount of a certain reagent is detected to become smaller than a predetermined minimum amount, it is necessary to supplement a new reagent. For instance, Japanese Patent Application Laid-Open Publication No. 2,966/80, discloses an apparatus for detecting an amount of a residual reagent in a reagent bottle. This known apparatus comprises a detecting float to be put in the reagent bottle and two arrays of detector groups which detect a position of the float in the reagent bottle. This apparatus has drawbacks in that the construction is complicated and it is not suitable for detecting a small amount of the residual reagent. Particularly, in a multi-item analyzer in which a plurality of reagents are set for effecting a plurality of test items, there must be provided a plurality of the detecting apparatuses and thus, the construction becomes further complicated.

SUMMARY OF THE INVENTION

The present invention's main objective is to provide an apparatus for detecting a residual amount of a liquid contained in a vessel in an accurate manner with a simple construction.

It is another object of the invention to provide an apparatus which can detect residual amounts of a plurality of liquids contained in different vessels.

According to the invention, an apparatus for detecting a residual amount of a liquid to be delivered by a delivery nozzle which is moved downward to the immersed into the liquid comprises means for detecting a distance along which the nozzle is moved downward from a reference level until the tip of nozzle is immersed into the liquid; and means for mathematically processing said distance to calculate a residual amount of the liquid.

BRIEF DESCRIPTION OF THE DRAWINGS

FIGS. 5 and 6 are plan views illustrating two embodiments of a display panel provided in a display unit of the apparatus shown in FIG. 2.

DESCRIPTION OF THE PREFERRED EMBODIMENTS

Figure 1:
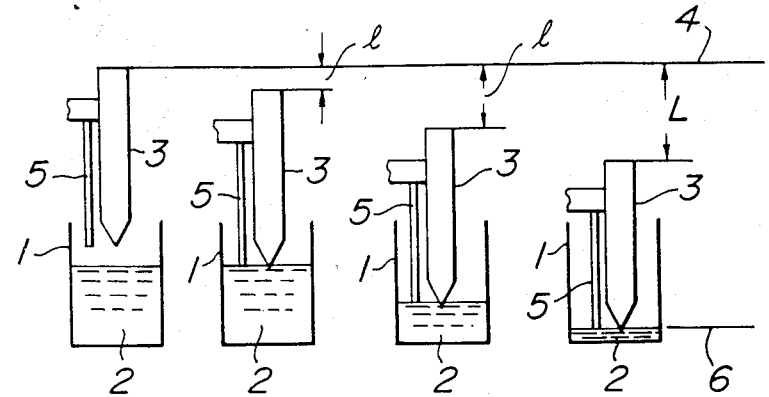
FIG. 1 is a schematic view showing a principal construction of the residual amount detecting apparatus according to the invention.

FIG. 1 shows a principal construction of the apparatus for detecting an amount of a residual liquid according to the invention. In FIG. 1, a vessel 1 contains a liquid 2 to be delivered by a delivery nozzle 3. The liquid 2 may be a reagent for effecting a test in a chemical analyzer. The nozzle 3 is moved downward at a constant speed from a reference level 4 into the reagent 2. To the nozzle 3 is secured a liquid-level detecting electrode 5 in such a manner that the tip of nozzle 3 slightly projects beyond the tip of electrode 5. Therefore, a liquid level detection signal is produced when the tip of nozzle 3 is immersed into the liquid 2. Alternatively, the detecting electrode 5 may be situated at the same level as the tip of the nozzle 3. With this structure, a liquid level detection signal is produced when the tip of the nozzle 3 contacts the surface of the liquid 2. According to the invention, a distance l along which the nozzle 3 has been moved from the reference level 4 until the tip of nozzle 3 contacts or is immersed into the liquid 2 is measured. As clearly shown in FIG. 1, this distance l corresponds to the liquid level and thus an amount of the liquid 2 remaining in the bottle 1. That is to say, if a large amount of the liquid 2 is remaining in the bottle 1, the distance l becomes shorter, whereas if the bottle 1 contains a smaller amount of the liquid 2, the distance l becomes longer. Further, there is defined a lowest standard level 6 of the residual liquid 2 corresponding to the predetermined maximum distance L and when a measured distance l becomes equal to the maximum distance L, it is judged or assumed that a sufficient amount liquid is not remaining in the bottle 2. By determining the lowest standard level 6, the accurate detection can be effected without being affected by any fluctuation in the position or level of the bottom of bottle 1 and of a rack of which the bottle 1 is placed.

Figure 2:
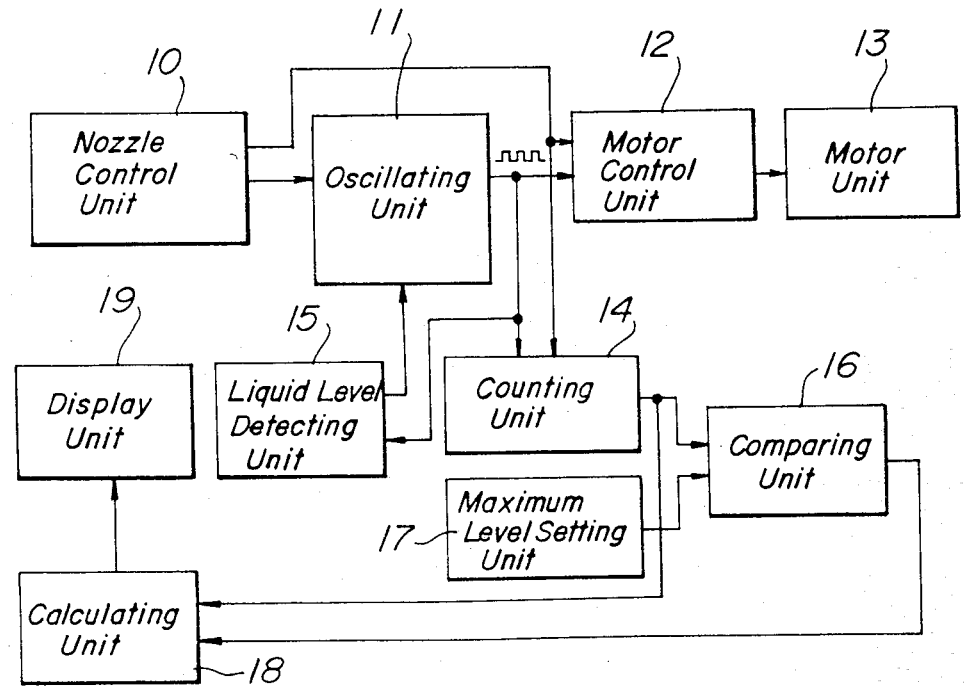
FIG. 2 is a block diagram illustrating an embodiment of the apparatus according to the invention.

FIG. 2 is a block diagram illustrating an embodiment of a circuitry of the apparatus for detecting an amount of a residual liquid according to the invention. When a nozzle control unit 10 receives a delivery command from a center control unit not shown, it produces a start signal which is then supplied to an oscillating unit 11. The oscillating unit 11 produces clock pulses having a given period in response to the start signal and the clock pulses are supplied to a motor control unit 12 which drives a motor 13 for moving the nozzle 3 downward at a given constant speed. The clock pulses generated from the oscillating unit 11 are also supplied to a counter unit 14 which is reset by the start signal supplied from the nozzle control unit 10 to initiate the up-count of clock pulses as soon as the nozzle 3 is moved downward. It should be noted that the counter unit 14 may down-count the clock pulses and in this case a suitable count value may be preset in the counter unit in response to the start signal.

The nozzle 3 is moved downward and when the electrode 5 contacts with the liquid or the nozzle tip is immersed in the liquid 2 to a given small extent, a liquid level detecting unit 15 including the liquid-level detecting electrode 5 produces a stop signal. In response to the stop signal, the oscillating unit 11 is disabled to stop the supply of clock pulses. Therefore, the counting unit 14 has counted the clock pulses which were produced during a time interval from the start signal corresponding to the initiation of the downward movement of the nozzle 3 to the stop signal corresponding to the immersion of the tip of nozzle 3 into the liquid and thus, the number of clock pulses counted by the counting unit 14 corresponds to a distance l over which the nozzle 3 has moved downward from the reference level 4. The count value thus obtained is supplied to one input of a comparing unit 16, the other input of which is supplied from a maximum distance setting unit 17 that inputs a maximum count value corresponding to the maximum distance L. As explained above, the maximum distance L corresponds to the minimum liquid-level 6. Therefore, by deriving a difference between the actual count value and the maximum count value from the comparing unit 16, it is possible to detect a depth (L-l) of the residual liquid 2 still remaining in the bottle 1. This difference is further supplied to a calculating unit 18 to calculate the residual amount of the liquid 2 in the bottle 1 or the number of times by which the liquid 2 can be delivered without supplementing a new liquid. The residual amount of liquid can be the depth of liquid remaining in the vessel. If the cross-sectional area of the vessel 1 is known, then the volume of liquid in the vessel can be determined by those skilled in the art by multiplying the cross-sectional area by the depth of liquid. The calculated amount or number of times is indicated on a display panel provided in a display unit 19. After a residual amount (i.e., the depth or volume) of liquid is determined, the nozzle 3 withdraws a specified unit amount of liquid for effecting a test in a chemical analyzer.

According to the present invention, since an amount of the liquid 2 remaining in the bottle 1 can be measured every time a delivery is effected and thus, it is possible to obtain useful data for managing or controlling the liquid, particularly the reagent for use in a chemical analyzer.

Figure 3:
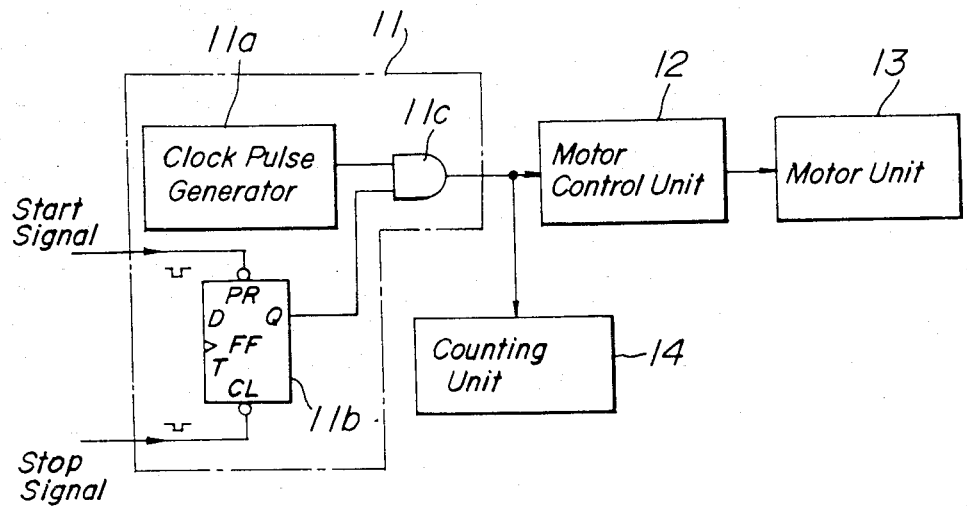
FIG. 3 is a circuit diagram showing an embodiment of an oscillating unit of the apparatus shown in FIG. 2.

FIG. 3 is a circuit diagram of an embodiment of the oscillating unit 11. In this embodiment, the motor unit 13 for driving the nozzle 3 comprises a stepping motor. The oscillating unit 11 comprises a clock pulse generator 11a, a flip-flop 11b and an AND gate 11c. The flip-flop 11b is set by the start signal supplied from the nozzle control unit 10 to make the AND gate 11c to pass the clock pulses continuously produced from the clock pulse generator 11a. When the liquid level detecting unit 15 produces the stop signal to reset the flip-flop 11b, the AND gate 11c is disabled to stop the passage of clock pulses. In this manner, the AND gate 11c can transmit the clock pulses during a time interval from the start signal to the stop signal and thus, the number of transmitted clock pulses corresponds to a distance l over which the nozzle 3 moves downward.

Figure 4:
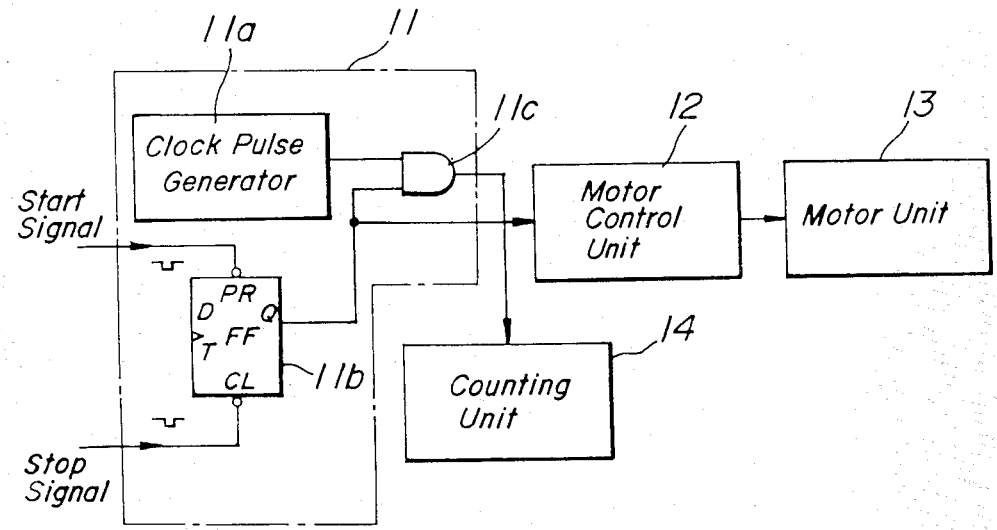
FIG. 4 is a circuit diagram depicting another embodiment of the oscillating unit.

FIG. 4 is a circuit diagram showing another embodiment of the oscillating unit 11. In this embodiment, the motor unit 13 comprises a D.C. or A.C. motor. Also in this embodiment, the oscillating unit 11 comprises a clock pulse generator 11a, flip-flop 11b and an AND gate 11c, however, the clock pulses which pass through the AND gate 11c are not supplied to the motor control unit 12, but are supplied only to the counting unit 14 and a Q output signal from the flip-flop 11b is supplied to the motor control unit 12.

According to the invention, a residual amount of a liquid, e.g. reagent can be detected in the manner mentioned above. Since a unit amount of the reagent required for effecting a single test is known, it is possible to derive the number of tests which may be effected by the residual reagent by dividing the residual amount by the unit amount in the calculating unit 18.

FIG. 5 is a plan view showing an embodiment of the display panel of the display unit 19 in which the numbers of a plurality of tests to be effected by residual amounts of a plurality of reagents can be displayed. In a first row 19a there are described test items such as GOT, GPT, TP, ALB, CRE, in a second row 19b there are displayed residual amounts of first reagents in the form of the numbers of tests and in a third row 19c there are indicated residual amounts of second reagents in the form of the numbers of tests which may be effected by using the residual second reagents. It should be noted that a mark "-" in the third row 19c represents that the relevant test item does not require a second reagent. If a test item requires a third reagent there may be provided a fourth row in the display panel. Those skilled in the art would recognize that the display panel could be arranged in columns rather than rows.

FIG. 6 is a plan view illustrating another embodiment of the display panel of the display unit 19. In this embodiment, a first row 19a' does not show the test items. Rather, the first row 19a shows indices representing numbers of samples, reagents or abbreviations. In a second row 19b' there are indicated the residual amounts of the liquids in the form of the numbers of tests which may be effected by using the residual liquids. It should be noted that the display unit 19 may further comprise a printer for printing the displayed numbers of tests which may be carried out with the aid of residual liquids. Further, when a residual amount of a liquid is decreased lower than the predetermined minimum amount, an alarm may be produced by an alarm lamp or buzzer.

As explained above, residual amounts of a plurality of reagents may be displayed on the display unit 19. In this case, when any one of a plurality of reagent bottles may be selectively positioned at a single delivery position and any desired reagent may be delivered by means of a single delivery nozzle, it is possible to detect residual amounts of all the reagents by means of the single detecting apparatus and thus, the construction can be made extremely simple.

According to the invention, since the liquid-level detecting signal supplied from the liquid-level meter, which has been usually provided in the delivery unit, can be utilized to detect a residual amount of liquid and any separate detecting mechanism is not required, the construction of the detecting apparatus becomes very simple. Further, since the residual amount of the liquid is detected every time the relevant liquid is delivered, it is possible not only to detect whether or not there is a liquid larger than a given amount, but also to detect accurately the residual amount itself. Therefore, total control of operations of the analyzer such as supplement of liquid and analytical processes can be effected precisely and simply. Moreover, in case of delivering a plurality of reagents with the aid of the single delivery nozzle, it is possible to detect residual amounts of all the liquids by means of the single detecting apparatus and therefore, the construction of the detecting apparatus can be further simplified.

What is claimed is:

1. An apparatus for detecting a residual amount of a liquid to be delivered by a delivery nozzle which is moved downward into contact with the surface of the liquid for selectively withdrawing a portion of the liquid, said apparatus comprising:

means for detecting a distance along which the nozzle is moved downward from a reference level until the tip of the nozzle contacts the surface of the liquid; and calculating means for processing said detected distance to calculate a residual amount of the liquid, said calculating means comprising means for deriving a difference between said detected distance and a predetermined maximum distance, and a calculating unit to calculate the residual amount of the liquid from said difference.

2. An apparatus according to claim 1, wherein said distance detecting means comprises an oscillating unit which is activated in response to the initial downward movement of the delivery nozzle to generate clock pulses having a given constant period until the tip of said delivery nozzle contacts the liquid and a counting unit for counting the clock pulses to produce a count value corresponding to said distance.

3. An apparatus according to claim 2, wherein said oscillating unit is activated by a start signal supplied from a nozzle control unit in response to a delivery command and is disabled in response to a stop signal which is generated by a liquid-level detecting unit when the nozzle tip contacts the liquid.

4. An apparatus according to claim 3, wherein said oscillating unit comprises a clock pulse generator for producing the clock pulses, a flip-flop which is set into a first condition to produce an enabling signal in response to said start signal and is set into a second condition in response to said stop signal to produce a disabling signal, and an AND gate having a first input connected to an output of the clock pulse generator and a second input connected to an output of said flip-flop so as to pass the clock pulses during a time interval from the start signal to the stop signal.

5. An apparatus according to claim 4, wherein said clock pulses are also supplied to a stepping motor for moving the delivery nozzle downward.

6. An apparatus according to claim 4, wherein said enabling signal is supplied to a D.C. or A.C. motor for moving the delivery nozzle downward.

7. An apparatus according to claim 1, wherein said difference detecting means comprises a unit for setting the maximum distance and a comparing unit for comparing the detected distance with the maximum distance to derive the difference therebetween.

8. An apparatus according to claim 1, wherein said difference detecting means comprises a preset counter in which a predetermined count corresponding to the maximum distance is preset at the start of the counting operation and which down-counts clock pulses having a given period while the delivery nozzle is moved downward until the nozzle tip contacts the liquid and said difference is derived as a count value at the end of the downward movement.

9. An apparatus according to claim 1, wherein said calculating means comprises a dividing circuit for dividing the residual amount by a unit amount which is delivered by a single delivery operation with the aid of the delivery nozzle to derive the number of times by which the liquid may be delivered.

10. An apparatus according to claim 9 further comprising means for displaying said derived number of times by which the liquid may be delivered.

11. An apparatus according to claim 10, wherein said displaying means comprises a display panel which includes a first rows indicating a plurality of different kinds of liquids and a second row indicating the number of times each respective liquid may be delivered.

12. The apparatus according to claim 11, wherein said plurality of different kinds of liquid are reagents for effecting different test items in a chemical analyzer and said first column indicates the test item.

13. An apparatus according to claim 1, wherein the delivery nozzle is immersed into the liquid.

* * * * *

UNITED STATES PATENT AND TRADEMARK OFFICE
CERTIFICATE OF CORRECTION

PATENT NO. : 4,502,126

DATED : February 26, 1985

INVENTOR(S) : Fumio Mizoguchi

It is certified that error appears in the above-identified patent and that said Letters Patent is hereby corrected as shown below:

On the title page

In the Foreign Application Priority Data, change "56-72793" to -- 56-72493 --.

Signed and Sealed this

Nineteenth Day of January, 1988

Attest:

DONALD J. QUIGG

Attesting Officer

Commissioner of Patents and Trademarks